(12) United States Patent
Fitts, Jr. et al.

(10) Patent No.: US 8,003,553 B2
(45) Date of Patent: Aug. 23, 2011

(54) ELASTIC-POWERED SHRINK LAMINATE

(75) Inventors: James Russell Fitts, Jr., Gainesville, GA (US); Janis Wilson Hughes, Alpharetta, GA (US); Patricia Hwang Calhoun, Alpharetta, GA (US); Wing-Chak Ng, Suwanee, GA (US); Glynis Allicia Walton, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 601 days.

(21) Appl. No.: 11/589,669

(22) Filed: Oct. 30, 2006

(65) Prior Publication Data

US 2007/0141354 A1 Jun. 21, 2007

Related U.S. Application Data

(60) Provisional application No. 60/750,645, filed on Dec. 15, 2005.

(51) Int. Cl.
*B32B 5/26* (2006.01)
*B32B 27/12* (2006.01)
*A61F 13/15* (2006.01)
*A61F 13/72* (2006.01)

(52) U.S. Cl. ........ 442/394; 442/329; 442/366; 442/381; 604/358; 604/396

(58) Field of Classification Search .................. None
See application file for complete search history.

(56) References Cited

U.S. PATENT DOCUMENTS

| | | | |
|---|---|---|---|
| 3,214,323 A | 10/1965 | Russell et al. | |
| 3,272,898 A | 9/1966 | Knee | |
| 3,331,728 A | 7/1967 | Lane | |
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,546,056 A | 12/1970 | Thomas | |
| 3,597,299 A | 8/1971 | Thomas | |
| 3,622,434 A | 11/1971 | Newman | |
| 3,692,618 A | 9/1972 | Dorschner et al. | |
| 3,802,817 A | 4/1974 | Matsuki et al. | |
| 3,849,241 A | 11/1974 | Butin et al. | |
| 3,925,127 A | 12/1975 | Yoshioka | |
| 4,133,924 A | 1/1979 | Seino et al. | |

(Continued)

FOREIGN PATENT DOCUMENTS

DE 22 23 780 11/1973

(Continued)

OTHER PUBLICATIONS

Co-pending U.S. Appl. No. 09/871,118, filed May 31, 2001.

(Continued)

*Primary Examiner* — Jennifer A Chriss
(74) *Attorney, Agent, or Firm* — Dority & Manning, P.A.

(57) ABSTRACT

An elastic-powered shrink laminate includes a shrinkable layer and an elastic layer bonded together while the elastic layer is in a dimensionally unstable, stretched state. The elastic layer remains substantially in the stretched state prior to shrinkage of the shrinkable layer. When the shrinkable layer is activated, the laminate retracts, and the retraction is aided (i.e. powered) by the elastic layer. The elastic-powered shrink laminate is useful in personal care absorbent articles where latent, post-assembly retraction of a waistband region is desired.

25 Claims, 4 Drawing Sheets

U.S. PATENT DOCUMENTS

| | | | |
|---|---|---|---|
| 4,340,563 A | 7/1982 | Appel et al. |
| 4,552,795 A | 11/1985 | Hansen et al. |
| 4,560,372 A | 12/1985 | Pieniak |
| 4,640,859 A | 2/1987 | Hansen et al. |
| 4,665,306 A | 5/1987 | Roland et al. |
| 4,762,521 A | 8/1988 | Roessler et al. |
| 4,842,596 A | 6/1989 | Kielpikowski et al. |
| 5,032,121 A | 7/1991 | Mokry |
| 5,057,368 A | 10/1991 | Largman et al. |
| 5,069,970 A | 12/1991 | Largman et al. |
| 5,108,820 A | 4/1992 | Kaneko et al. |
| 5,108,827 A | 4/1992 | Gessner |
| 5,171,239 A | 12/1992 | Igaue et al. |
| 5,207,664 A | 5/1993 | Blanco |
| 5,257,982 A | 11/1993 | Cohen et al. |
| 5,272,236 A | 12/1993 | Lai et al. |
| 5,277,976 A | 1/1994 | Hogle et al. |
| 5,294,482 A | 3/1994 | Gessner |
| 5,322,728 A | 6/1994 | Davey et al. |
| 5,336,552 A | 8/1994 | Strack et al. |
| 5,376,198 A | 12/1994 | Fahrenkrug et al. |
| 5,385,775 A | 1/1995 | Wright |
| 5,422,172 A | 6/1995 | Wu |
| 5,466,410 A | 11/1995 | Hills |
| 5,482,772 A | 1/1996 | Strack et al. |
| 5,491,016 A | 2/1996 | Kaiser et al. |
| 5,514,470 A | 5/1996 | Haffner et al. |
| 5,536,555 A | 7/1996 | Zelazoski et al. |
| 5,567,501 A | 10/1996 | Srinivasan et al. |
| 5,571,619 A | 11/1996 | McAlpin et al. |
| 5,643,240 A | 7/1997 | Jackson et al. |
| 5,674,211 A | 10/1997 | Ekdahl |
| 5,679,042 A | 10/1997 | Varona |
| 5,700,255 A | 12/1997 | Curro et al. |
| 5,707,468 A | 1/1998 | Arnold et al. |
| 5,789,328 A | 8/1998 | Kurihara |
| 5,804,021 A | 9/1998 | Abuto et al. |
| 5,814,178 A | 9/1998 | Jacobs |
| 5,830,555 A | 11/1998 | Srinivasan et al. |
| 5,851,935 A | 12/1998 | Srinivasan et al. |
| 5,873,868 A | 2/1999 | Nakahata |
| 5,883,028 A | 3/1999 | Morman et al. |
| 5,906,879 A | 5/1999 | Huntoon et al. |
| 5,914,184 A | 6/1999 | Morman |
| 5,990,377 A | 11/1999 | Chen et al. |
| 6,001,303 A | 12/1999 | Haynes et al. |
| 6,018,093 A | 1/2000 | Roe et al. |
| 6,168,585 B1 | 1/2001 | Cesco-Cancian |
| 6,217,889 B1 | 4/2001 | Lorenzi et al. |
| 6,491,777 B1 | 12/2002 | Bevins et al. |
| 6,491,928 B1 | 12/2002 | Smith, III |
| 6,503,431 B1 | 1/2003 | Kasai et al. |
| 6,613,033 B1 | 9/2003 | Popp et al. |
| 6,663,611 B2 | 12/2003 | Blaney et al. |
| 2002/0086602 A1* | 7/2002 | Friderich et al. ............. 442/366 |
| 2004/0005834 A1 | 1/2004 | Zhou et al. |
| 2004/0107481 A1 | 6/2004 | Montell et al. |
| 2004/0126518 A1* | 7/2004 | Mendes et al. ............. 428/34.8 |
| 2004/0158217 A1 | 8/2004 | Wu et al. |
| 2005/0131382 A1 | 6/2005 | Brud et al. |
| 2005/0148980 A1 | 7/2005 | Fitton |

FOREIGN PATENT DOCUMENTS

| | | |
|---|---|---|
| DE | 195 23 497 A1 | 1/1997 |
| EP | 0 211 197 | 2/1987 |
| EP | 0 330 716 A2 | 9/1989 |
| EP | 0 687 757 A2 | 12/1995 |
| EP | 0 586 924 B1 | 10/1997 |
| EP | 0 617 940 | 11/1999 |
| GB | 783726 | 9/1957 |
| GB | 1 293 456 | 10/1972 |
| GB | 2 160 817 A | 1/1986 |
| GB | 2 284 786 A | 6/1995 |
| JP | 06031869 | 2/1994 |
| JP | 08176947 | 12/1994 |
| JP | 8-176947 | 7/1996 |
| WO | WO 00/38918 | 7/2000 |
| WO | WO 01/87589 | 11/2001 |
| WO | WO 2005/030090 | 4/2005 |
| WO | WO 2006/118838 A2 | 11/2006 |

OTHER PUBLICATIONS

Co-pending U.S. Appl. No. 09/871,171, filed May 31, 2001.
A.A. Burgeni and C. Kapur, Capillary Sorption Equilibria in Fiber Masses, *Textile Research Journal*, vol. 37, May 1967, pp. 356-366.

* cited by examiner

ELASTIC-POWERED SHRINK LAMINATE

CROSS REFERENCE TO RELATED APPLICATION

This application claims the benefit of U.S. Provisional Application No. 60/750,645, filed 15 Dec. 2005.

BACKGROUND OF THE INVENTION

This invention is directed to an elastic-powered shrink laminate including a stretched elastic layer bonded to a heat shrinkable layer.

Personal care absorbent articles, such as training pants, adult incontinence articles, swimwear and some diapers, advantageously include a waistband that shrinks when heated. In one example, a waistband may include an elastic layer laminated between two nonwoven facing layers when the elastic layer is in a stretched state. For reasons relating to equipment and processing, the waistband remains in a substantially flat, extended state during manufacture of the absorbent article. Once the garment has been formed, the waistband is heated to cause shrinkage of the waistband. When the waistband shrinks, it pulls in the other materials to which it is laminated, enabling the absorbent article to properly and comfortably fit the wearer.

In the past, it has been difficult to provide waistband materials which have both heat shrinkage and significant elastic properties. If a material is elastic, it tends to recover to a dimensionally stable, retracted state at ambient temperature, and tends not to retract further upon heating. If a material is heat shrinkable, it tends to a) remain in a dimensionally unstable stretched state prior to heating, b) retract to a dimensionally stable unstretched state only after heating, and c) behave as an inelastic material at its dimensionally stable state after retraction and cooling. While polymer combinations have been developed to provide both elasticity and heat shrinkage, the properties tend to oppose each other such that greater elasticity coincides with insufficient heat shrinkage, and greater heat shrinkage coincides with insufficient elasticity. There is a need or desire for a better hybrid material that exhibits sufficient elasticity and heat shrinkage, for use in waistbands of personal care absorbent articles.

SUMMARY OF THE INVENTION

The present invention is directed to an elastic-powered shrink laminate including a heat shrinkable layer and an elastic layer. The heat shrinkable layer and elastic layer are bonded together when the elastic layer is in a dimensionally unstable, stretched state. The heat shrinkable layer, elastic layer and bonding are configured and designed so that the elastic layer remains substantially in the stretched state prior to shrinkage of the heat shrinkable layer.

When the laminate is heated to an activation temperature of the heat shrinkable layer, the heat shrinkable layer shrinks, and the shrinkage is powered by retraction of the elastic layer. The powering by the elastic layer may cause the heat shrinkable layer to shrink more rapidly and/or to a greater extent than it otherwise would.

The elastic-powered shrink laminate may or may not behave as an elastic laminate after shrinking and subsequent cooling of the heat shrinkable layer. If the elastic layer recovers to about the same extent that the heat shrinkable layer retracts, then the resulting laminate may have limited elasticity due to the relative inelasticity of the heat shrinkable layer. A laminate prepared in this fashion may then be rendered elastic by subsequent mechanical stretching, or manual stretching during use, of the laminate material. Alternatively, the heat shrinkable layer may be elastic or easily stretchable after shrinkage, and the resulting laminate may have adequate elasticity without further processing.

If the elastic layer recovers to a sufficiently greater extent than the heat shrinkable layer retracts, then the elastic layer may intermittently separate from the heat shrinkable layer and cause gathering of the heat shrinkable layer between the bonded regions. In this embodiment, the resulting laminate may behave as an elastic laminate without requiring subsequent mechanical stretching or manual stretching of the laminate and its heat shrunk layer. Such subsequent stretching may be employed to further increase the elastic stretch and recovery of the laminate.

By proper selection and design of the heat shrinkable and elastic layers, an elastic-powered shrink laminate can be prepared which has any desired amount of heat shrinkage, and any desired amount of elasticity subsequent to the heat shrinkage. Because the heat shrinkage and elasticity are contributed by different layers, the heat shrinkage and elasticity can coexist in the laminate to a greater extent than was previously possible with hybrid materials formed of a single polymer or polymer combination.

With the foregoing in mind, it is a feature and advantage of the invention to provide an elastic-powered shrink laminate having a tailored amount of heat shrinkage and a tailored amount of elasticity.

It is also a feature and advantage of the invention to provide an elastic-powered shrink laminate having more rapid and/or greater heat shrinkage than conventional elastic or heat shrinkable materials.

It is also a feature and advantage of the invention to provide a personal care absorbent article which incorporates the elastic powered shrink laminate in a waistband material.

DEFINITIONS

The term "activation temperature" refers to a minimum elevated temperature (above ambient temperature) which initiates the shrinkage of a heat shrinkable material. This is often a temperature at which the polymer molecules begin to soften, allowing the molecules to return from a higher energy "oriented" state to a lower energy "random" state, and allowing the material to retract from a stretched dimension toward a pre-stretched dimension. Heat shrinkable materials will shrink at or above the activation temperature, but are typically maintained below the temperature where the material melts or otherwise loses its integrity.

The term "continuous filaments" refers to strands of continuously formed polymeric filaments. Such filaments will typically be formed by extruding molten material through a die head having a certain type and arrangement of capillary holes therein.

The term "elastic," "elasticized," or "elastomeric" refers to a material which, upon application of a stretching force, is stretchable to a stretched length at least about 25 percent greater than its relaxed length at 25° C., i.e., can be stretched to at least about one and one-quarter times its relaxed length, and upon release of the stretching force will recover at least about 40 percent of the elongation at 25° C., i.e., will, in the case of 25% elongation, contract to an elongation of not more than about 15%. For example, a 100 centimeter length of material will, under the foregoing definition, be deemed to be elastic if it can be stretched to a length of at least 125 centimeters and if, upon release of the stretching force, it contracts, in the case of being stretched to 125 cm, to a length of not more than about 115 centimeters. Many elastic materials used in the practice of the invention can be stretched to a stretched length at least 50% greater, or at least 75% greater, or at least 100% greater than their relaxed length. Many elastic materials, upon release of the stretching force, will recover at least 50% of the elongation, or at least 75% of the elongation, or at least 90% of the elongation, or about 100% of the elongation.

The term "film" refers to a polymer sheet or layer formed using a film forming process such as cast extrusion, blown extrusion, extrusion coating or the like.

The term "heat shrinkable" refers to a material that will shrink in at least one direction when it is heated to an elevated activation temperature or higher, but will not exhibit corresponding shrinkage at ambient temperature. For example, a heat shrinkable material having a length of 100 cm may shrink by at least 20% (to a length of 80 cm), or by at least 25% (to a length of 75 cm), or by at least 33% (to a length of 67 cm), or by at least 50% (to a length of 50 cm) when heated to its activation temperature or higher. Whether or not a material is heat shrinkable depends both on the polymer(s) used to make the material and how the material is made. Often, a heat shrinkable material is made by a) forming a film or other layer from a suitable polymer, b) stretching the material at or above its activation temperature, c) cooling the material while maintaining the stretched configuration, and d) removing the stretching force. The heat shrinkable material so made will maintain its stretched configuration until it is again heated to its activation temperature, at which time the material will retract toward its original pre-stretched dimension. Some heat shrinkable materials may be made by stretching the film or other layer at ambient temperature, or below the activation temperature, and will maintain the stretched configuration until heated to or above the activation temperature.

The term "latent," "latent elasticity," or variation thereof refers to materials having a certain degree of stretchability which are capable of becoming more stretchable upon activation, e.g. by heat activation, microwave, ultrasound, chemical treatment, and so forth. The materials may or may not be elastic prior to activation, but will be elastic after activation.

The term "nonelastic" or "inelastic" refers to any material which does not fall within the definition of "elastic" above.

The term "polymer" or "polymeric" generally includes, but is not limited to, homopolymers, copolymers, such as, for example, block, graft, random and alternating copolymers, terpolymers, etc. and blends and modifications thereof. Furthermore, the term "polymer" includes all possible geometrical configurations of the material, such as isotactic, syndiotactic and random symmetries.

The terms "machine direction" or "MD" means the direction along the length of a fabric in the direction in which it is produced. The terms "cross machine direction," "cross directional," or "CD" mean the direction across the width of fabric, i.e. a direction generally perpendicular to the MD.

The term "nonwoven web" refers to a web having a structure of individual fibers or threads that are interlaid, but not in an identifiable, repeating manner. Nonwoven webs have been, in the past, formed by a variety of processes such as, for example, meltblowing processes, spunbonding processes and bonded carded web processes.

The term "meltblown" or "meltblown fibers" means fibers formed by extruding a molten thermoplastic material through a plurality of fine, usually circular, die capillaries as molten thermoplastic material or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, U.S. Pat. No. 3,849,241 to Butin, which is incorporated herein in its entirety by reference thereto.

The term "spunbond" or "spunbonded fibers" refers to small diameter fibers formed by extruding a molten thermoplastic material as filaments from a plurality of fine, usually circular, capillaries of a spinerette with the diameter of the extruded filaments then being rapidly reduced as by, for example, eductive stretching or other well-known spunbonding mechanisms. The production of spunbonded nonwoven webs is illustrated in patents such as, for example, U.S. Pat. No. 4,340,563 to Appel et al., and U.S. Pat. No. 3,692,618 to Dorschner et al. The disclosures of these patents are incorporated by reference.

The term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern through the web and/or alternatively the web may be bonded across its entire surface if so desired. When using bicomponent staple fibers, through-air bonding equipment is, for many applications, especially advantageous.

The term "retraction potential" refers to the maximum potential shrinkage of a heat shrinkable material, i.e. the maximum amount of shrinkage that will result if a heat shrinkable material is heated to or above its activation temperature, and is not restrained from shrinking. For instance, a heat shrinkable material having a length of 100 cm in any one direction has a retraction potential of 33% if it shrinks to a length of 67 cm when heated to or above its activation temperature, without restraint. Some heat shrinkable materials shrink only partially at the activation temperature, and reach maximum shrinkage only when heated to a somewhat higher temperature. In these instances, the "retraction potential" refers to the maximum potential shrinkage at the higher temperature.

The term "recovery potential" refers to the maximum potential recovery of an elastic material which is being maintained in a stretched state at 25° C., when all restraining forces are removed. For instance, an elastic material that is initially maintained at a stretched length of 100 cm in any one direction has a recovery potential of 33% if it recovers to a length of 67 cm at 25° C. when all restraining forces are removed.

The term "personal care absorbent article" refers to diapers, training pants, swimwear, absorbent underpants, adult incontinence products, feminine hygene products and the like.

DETAILED DESCRIPTION OF THE INVENTION

Figure 1:
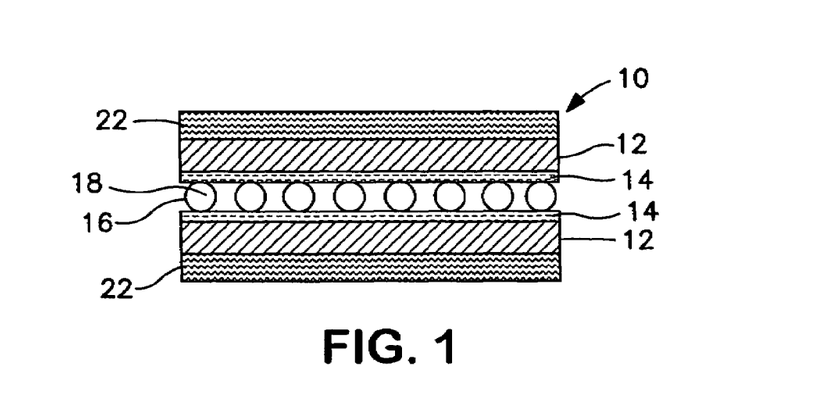
FIG. 1 is a sectional view of an elastic-powered shrink laminate of the invention, illustrating both essential and optimal layers.
Figure 2:
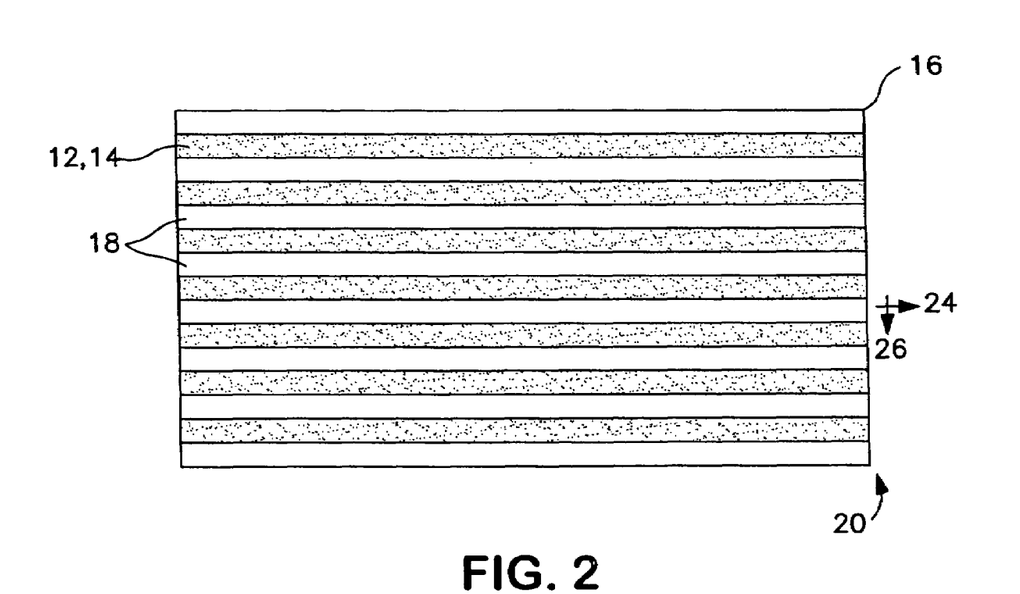
FIG. 2 is a top plan view of an elastic-powered laminate of the invention, illustrating the essential layers.

Referring to FIGS. 1 and 2, an elastic-powered shrink laminate 10 (FIG. 1) or 20 (FIG. 2) includes at least a heat shrinkable layer 12 and an elastic layer 16. The heat shrinkable layer 12 and elastic layer 16 are bonded together when the elastic layer 16 is in a dimensionally unstable, stretched state, and the bonding may be accomplished by means of an adhesive layer 14.

The layers of the elastic-powered shrink laminate 10 or 20 are suitably configured and designed so that the elastic layer 16 remains substantially in the stretched state prior to shrinkage of the heat shrinkable layer. For end use applications such as personal care absorbent articles, it is desirable to maintain the elastic-powered shrink laminate in a flat (extended) configuration during manufacture and assembly of the article, and subsequently activate the laminate to cause shrinkage. To this end, the elastic layer 16 should not be so powerful or heavy relative to the remaining layers that the elastic layer dominates the laminate prior to the heat shrinking step, and causes premature retraction of the laminate.

One way of reinforcing the elastic layer 16 in the stretched state is to employ additional layers as shown in FIG. 1. The elastic layer 16 may, for instance, be positioned between two of the heat shrinkable layers 12 and bonded to each one by a separate adhesive layer 14. The heat shrinkable layers 12 may, in turn, be joined to outer facing layers 22, such as nonwoven webs or film/nonwoven laminates. When the laminate 10 is used as an elastic waistband in a personal care absorbent article, the facing layers 22 may constitute extensions of the bodyside liner and outer cover of the article.

Another way of reinforcing the elastic layer 16 in the stretched state is to form the elastic layer 16 of a relatively light, intermittent material and to form the heat shrinkable layer(s) 12 of a relatively heavy, uninterrupted material. In the embodiments shown in FIGS. 1 and 2, the elastic layer 16 is formed of spaced apart, nonintersecting, substantially parallel filaments 18 which are continuous only in a direction of stretching 24, and discontinuous in a mutually perpendicular direction 26. The elastic filaments 18 are disposed in the direction of stretching 24, which corresponds to a direction of orientation (and potential shrinkage) of the heat shrinkable layer 12. The heat shrinkable layer 12, by comparison, is suitably made from an uninterrupted polymer sheet, such as a film. Depending on the thickness and spacing of elastic filaments 18 shown in FIG. 2, for instance, the elastic filaments 18 may cover about 50% or less, or about 40% or less, or about 30% or less of the area covered by the heat shrinkable film 12.

Another technique for reinforcing the elastic layer 16 in the stretched state is to make sure the elastic filaments 18 (or other elastic material) are substantially continuously and strongly bonded to the heat shrinkable layer 12. This is suitably accomplished using a substantially continuous adhesive layer 14 to bond the elastic layer 16 to the heat shrinkable layer 12. If the bonding is discontinuous, the stretched elastic layer 16 will have a greater tendency to recover in the unbonded regions between the bonded regions, causing premature gathering of the remaining layer(s). While other bonding techniques may also be employed, adhesive bonding is considered to be more suitable. With thermal bonding, for instance, care must be taken to avoid premature shrinkage of the heat shrinkable layer 12. With ultrasonic bonding, care must be taken to avoid damaging or severing the elastic filaments 18.

Other techniques such as proper selection of polymers, basis weights and layer thicknesses, and amount of stretching of the elastic layer 16, will also influence the ability of the elastic-powered shrink laminate to maintain the elastic layer 16 substantially in the stretched state prior to shrinkage of the heat shrinkable layer 12. More than one of the foregoing techniques may be employed, in combination, to achieve this result. By "substantially in the stretched state," it is meant that the elastic layer 16 should retain a recovery potential of at least about 25%, suitably at least about 33%, or at least about 50%, in the elastic-powered shrink laminate before the heat shrinkage step has been performed. Prior to the heat shrinkage step, the elastic-powered shrink laminate should maintain a substantially flat configuration and should not be gathered by the elastic layer 16.

The heat shrinkable layer 12 can be a film, nonwoven web or other material, and is suitably a film. The film thickness may vary depending on whether one or two heat shrinkable layers are employed, whether additional outer facing layers are employed, and the retractive force exerted by the elastic layer 16. The heat shrinkable film may have a thickness of about 5-100 microns, suitably about 10-50 microns, or about 15-40 microns.

The heat shrinkable layer 12 may be designed with a polymer or polymer blend to provide an activation temperature of about 28-35° C., or about 35-55° C., or about 55-75° C., or higher. In one interesting embodiment, the heat shrinkable layer 12 may have an activation temperature of about 28-35° C., which is low enough to activate the shrinkage using the heat of a wearer's body. For instance, a wearer could don a personal care absorbent article which employs the elastic-powered shrink laminate as a waistband material. After the garment is donned, the heat from the wearer's body may cause the waistband to shrink to the extent required to obtain a comfortable fit.

In most instances, a higher activation temperature will be required in order for the elastic-powered laminate to withstand processing, packaging, transportation and storage without exhibiting premature shrinkage. An activation temperature of at least 55° C., or about 55-75° C., may be particularly suitable.

The heat shrinkable layer 12 should have a retraction potential of at least about 20%, or at least about 25%, or at least about 33%, or at least about 50%. This means that the heat shrinkable layer is capable of shrinking by a corresponding percentage in at least one direction when heated to its activation temperature or higher, and when no restraining force is applied which inhibits the retraction. The retraction potential of a heat shrinkable layer is typically related to the extent that the heat shrinkable layer remained stretched after formation, cooling and annealing. For example, a heat shrinkable film formed by stretching a precursor layer above its activation temperature to twice its pre-stretched length, and cooling the film at that length, may have a retraction potential of up to 50% based on its ultimate length.

A variety of thermoplastic polymers and polymer mixtures can be used to form the heat shrinkable layer 12. Suitable polymers and polymer mixtures include those which (when formed into a film or other layer) can be stretched, and which remain stretched below an activation temperature. Suitable polymers include without limitation ethylene homopolymers, ethylene-alpha olefin copolymers containing up to about 20% by weight of a $C_3$ to a $C_{12}$ alpha-olefin comonomer, propylene homopolymers, propylene copolymers containing up to about 20% by weight ethylene or a $C_4$ to $C_{12}$ alpha-olefin comonomer, amorphous poly-alpha olefins (e.g. propylene homopolymers made partially with atactic polypropylene, and certain copolymers of propylene with ethylene and/or butylenes), polyvinyl chlorides, and combinations thereof. These polymers may be blended with other polymers, such as elastic polymers, provided that the blend yields a layer 12 with suitable heat shrink properties. The heat shrinkable layer 12 may suitably have elastic properties after heat shrinkage, and the inclusion of elastic polymers facilitates these properties.

Single-site catalyzed olefin polymers, e.g. ethylene homopolymers and ethylene-alpha olefin copolymers, are particularly suitable for forming the heat shrinkable layer 12. These polymers exhibit rapid crystallization when the heat shrinkable layer is initially formed and cooled, and many of them have convenient activation temperatures between about 55-75° C. Both the polymer density and activation temperature of these polymers vary inversely with the level of alpha-olefin comonomer. Suitably, the polymer density is about 0.86-0.94 grams/cm$^3$, or about 0.90-0.935 grams/cm$^3$. If the comonomer content is too high and the density is too low, the activation temperature approaches ambient temperature and the polymer behaves more like an elastomer. Single-site catalyzed ethylene homopolymers and ethylene-alpha olefin copolymers are sold by ExxonMobil Chemical Co. under the trade names EXACT and EXCEED, and by Dow Chemical Co. under the trade names AFFINITY and ENGAGE.

The heat shrinkable layer may be a breathable film, which is permeable to water vapor but not aqueous liquids. A breathable film may have a water vapor transmission rate ("WVTR") of at least about 500 grams/m$^2$-24 hours, suitably at least about 1000 grams/m$^2$-24 hours, or about 1000-5000 grams/m$^2$-24 hours, measured using the WVTR test described herein. A breathable film can be prepared by mixing one or more of the foregoing polymers with about 25-75% by weight, or about 40-60% by weight of a suitable particulate filler (e.g. calcium carbonate), and stretching the resulting film in at least one direction to form micropores or microvoids around the filler particles. Techniques for making breathable films are known.

The elastic layer 16 may be a film or nonwoven web, but is suitably formed of spaced apart, nonintersecting, substantially parallel elastic filaments 18 as shown in FIGS. 1 and 2. The elastic layer 16 is stretched to a stretched length, suitably in one direction, before it is bonded to the heat shrinkable layer 16, and the stretched length is maintained during the bonding. The stretched length of layer 16 may be at least about 25% greater than an initial unstretched length, suitably at least about 33% greater, or at lest about 50% greater, or at least 100% greater. While the elastic layer 16 alone would be dimensionally unstable at the stretched length, the stretched length is maintained by bonding the elastic layer 16 to the heat shrinkable layer(s) 12.

The elastic layer 16 in the laminate should have a recovery potential which is at least as high as the retraction potential of the heat shrinkable layer(s) 12. If the recovery potential of elastic layer 16 is less than the retraction potential of heat shrinkable layer(s) 12, then the elastic layer 16 will not be able to retract as much as the heat shrinkable layer(s) 12 are activated. For instance, the elastic layer 16 should have a recovery potential of at least about 20% based on the stretched length, suitably at least about 25%, or at least about 33%, or at least about 50%.

As explained further below, with respect to FIGS. 3A-3D, the elastic properties of the laminate after shrinkage may be enhanced by providing the elastic layer 16 with a recovery potential that exceeds the retraction potential of the heat shrinkable layer(s) 12. For instance, the elastic layer 16 may have a recovery potential which is at least 1.2 times, suitably at least 1.33 times, or at least 1.5 times, or at least 2.0 times the retraction potential of the heat shrinkable layer(s) 12. During the heat shrinking step, the polymers of the heat shrinkable layer(s) 12 and adhesive layer(s) 14 are softened to an extent, permitting the elastic layer 16 to pull away from the heat shrinkable layer and retract further, causing localized gathering of the remaining layers in the laminate. The extent of the pulling away and gathering depends on the extent to which the recovery potential of the elastic layer exceeds the retraction potential of the heat shrinkable layer(s).

As explained above, elastic layer 16 is suitably formed of spaced apart elastic filaments 18. When in the stretched state, as shown in FIG. 2, the elastic filaments 18 may have diameters of about 0.1 mm to about 5.0 mm, or about 0.2-2.0 mm, or about 0.3-1.0 mm. The elastic filaments may be spaced apart (center-to-center) by a distance of at least 1.5 times their diameters, or at least twice their diameters, or at least three times their diameters or at least four times their diameters. The elastic filaments may have a frequency in the direction perpendicular to their elongation (in direction 26, FIG. 2) of about 1-15 filaments per centimeter, or about 3-10 filaments per centimeter, or about 5-8 filaments per centimeter.

The elastic layer 16 may be formed from a variety of elastic polymers. Suitable elastomers include without limitation styrene-diene block copolymers, styrene-olefin block polymers, polyurethanes, copolyether esters, polyamide-polyether block copolymers, ethylene-vinyl acetate copolymers, and combinations thereof. The elastomers may be combined with other polymers (e.g. polyolefins), provided that the polymer blend performs suitably as an elastomeric polymer in the elastic layer 16. Such polymer blends should include at least 50% elastomer, or at least 60% elastomer, or at least 75% elastomer. A low molecular weight polyolefin wax such as EPOLENE®C-10, sold by Eastman Chemical Co., may be present at about 5-25% by weight to aid in processing.

Particularly suitable elastic polymers and polymer blends are sold by Kraton Polymers LLC of Houston, Tex. under the trade name KRATON®. KRATON® polymers include styrene-diene block copolymers, for example styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G-1652, G-1657M, G-1730, D-1114, D-1116, and D-1102.

The adhesive layer (or layers) 14 can be formed of a hot melt or melt spray adhesive which a) provides a sufficiently strong bond between elastic layer 16 and heat shrinkable layer 12 to maintain elastic layer 16 in the stretched state prior to heat shrinkage, and b) can be applied substantially continuously over the interfacial regions between elastic layer 16 and heat shrinkable layer(s) 12. Suitable adhesives include without limitation styrene-isoprene-styrene block copolymer adhesives available from Bostic, Inc. of Wauwatosa, Wis. under the brand names H2096 and H2808-07. The adhesive may be applied to an inner surface of the heat shrinkable layer 12 and/or to the elastic layer 16 at a basis weight of about 1.5-7.5 grams/m$^2$, suitably about 2.0-4.0 grams/m$^2$. The adhesive, which suitably has elastic properties, may be applied using a melt spraying process or other suitable techniques such as brushing or extrusion film coating. The adhesive may cover at least 70% of an interfacial area between heat shrinkable layer 12 and elastic layer 16, suitably at least 80%, or at least 90%, or about 100%.

To enhance the adhesion, the elastic layer 16 (e.g. elastic filaments 18) may include tackifying resin combined with the elastomeric polymer. Particularly suitable tackifying resins include tackifiers based on hydrogenated styrene hydrocarbon resins and sold by Eastman Chemical Co. under the trade name REGALREZ®. Tackifiers may constitute up to about 40% by weight, suitably about 10-25% by weight of a polymer blend which includes the elastomer and tackifier.

As illustrated in FIG. 1, one or more facing layers 22 can be joined to the heat shrinkable layer(s) 12 on one or both sides of the laminate 10. Alternatively, a heat shrinkable layer 12 may be bonded on only one side of elastic layer 16, and a facing layer may be bonded to the elastic layer 16 on an opposing side. Alternatively, a facing layer 22 may be present on only one side of a laminate 10 which includes heat shrinkable layers 12 on both sides of elastic layer 16. Alternatively, facing layers 22 may be present on both sides of a laminate 10 which includes only one heat shrinkable layer 12. Alternatively, a facing layer 22 need not be present at all, and the laminate 10 may include a heat shrinkable layer 12 on one or both sides of the elastic layer 16.

Suitable facing layers 22 include without limitation nonwoven layers, such as spunbond webs, meltblown webs, bonded carded webs and combinations thereof. Also suitable for facing layers 22 are film/nonwoven laminates. Facing layers 22 can be bonded to the adjacent layers(s) using adhesive, thermal or ultrasonic bonding, and are suitably joined using an adhesive. In one embodiment, facing layers 22 are joined using the same type of adhesive, or the same adhesive, that is used to join heat shrinkable layer(s) 12 with elastic layer 16.

Figure 3A:
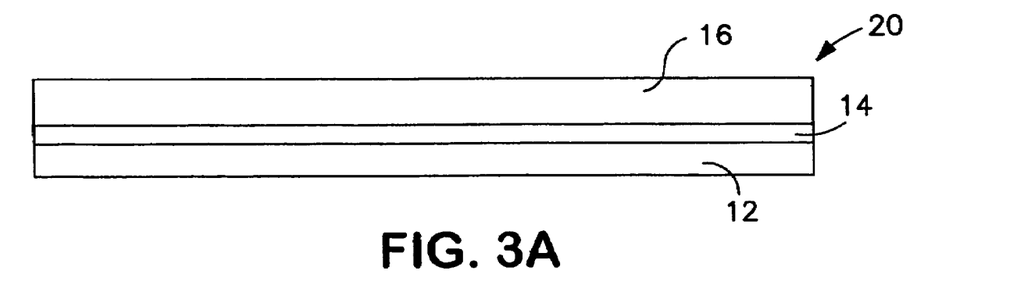
FIGS. 3(a), 3(b), 3(c) and 3(d) are front views of the elastic-powered laminate of FIG. 2, in different stages of processing, before and after heat shrinkage.
Figure 3B:
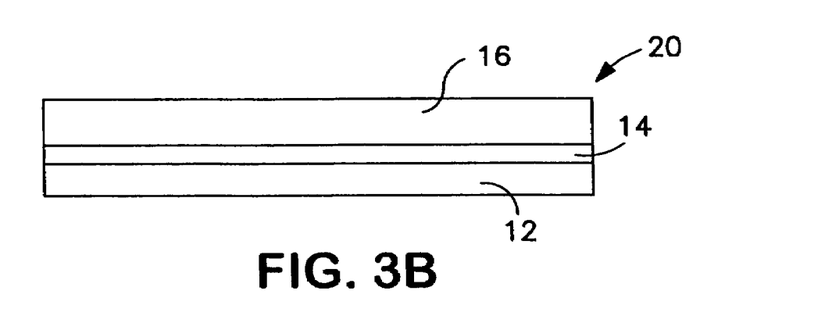
Figure 3C:
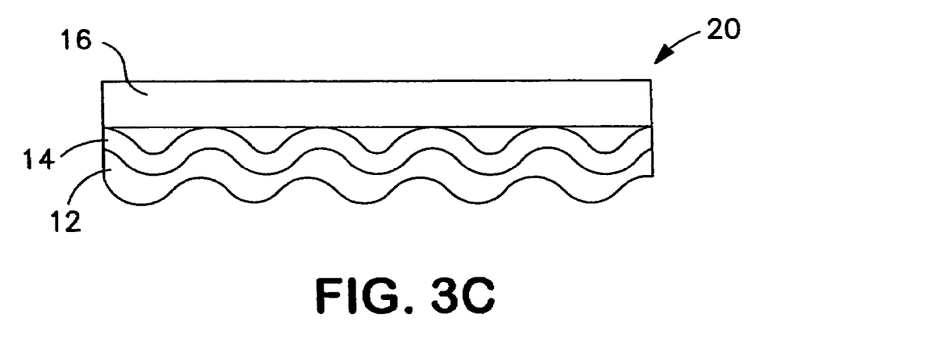
Figure 3D:
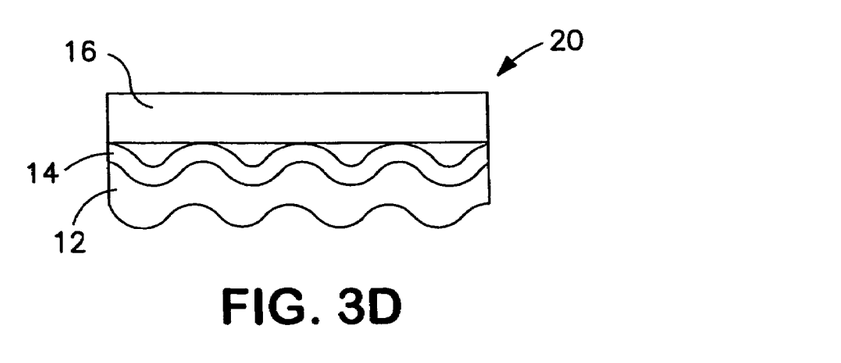

FIGS. 3A-3D schematically illustrate how heat shrinking the elastic-powered shrink laminate 20 of FIG. 2 may operate to produce an elastic or inelastic waistband laminate having a reduced overall length. FIG. 3A illustrates the elastic-powered shrink laminate having a first length prior to heat shrinkage. When the laminate 20 is heated to or above the activation temperature of heat shrinkable layer 12, the laminate 20 shrinks to a second, shorter length as shown in FIG. 3B or to a third, even shorter length as shown in FIG. 3D.

If the retraction potential of the heat shrinkable layer 12 is about the same as the recovery potential of the elastic layer 16, the laminate 20 may heat shrink to a second length shown in FIG. 3B, while the layers 12 and 16 remain substantially continuously bonded along their interfacial regions. At that point, the laminate 20 may be inelastic, because the recovered elastic layer 16 is restrained by the retracted heat shrinkable layer 12. The laminate 20 can then be "elasticized" (rendered elastic) by mechanically or manually stretching it, and permitting it to recover to the configuration shown in FIG. 3C. The stretching at ambient temperature will permanently elongate the layer 12. The subsequent retraction will either cause corrugation of the entire laminate, or will result in intermittent separation between the layers as shown in FIG. 3C, while the elastic layer 16 returns toward its dimensionally stable relaxed length. In either case, the laminate 20 will then be elastic. Alternatively, the retracted heat shrinkable layer 12 may be elastic, in which case the laminate 20 will be elastic without further processing.

If the recovery potential of the elastic layer 16 exceeds the retraction potential of the heat shrinkable layer 12, then the laminate 20 may shrink to an even shorter third length shown in FIG. 3D, whereupon the elastic layer 16 intermittently separates from the heat shrinkable layer 12 and recovers to a greater extent, causing corrugation of the retracted shrinkable layer 12. This laminate 20 will have elastic stretch and recovery properties without requiring further processing. However, the elastic stretch and recovery properties of the laminate 20 in FIG. 3D may be further enhanced by mechanically or manually stretching the laminate beyond the point where the layer 12 becomes flat, and allowing it to recover.

Figure 4:
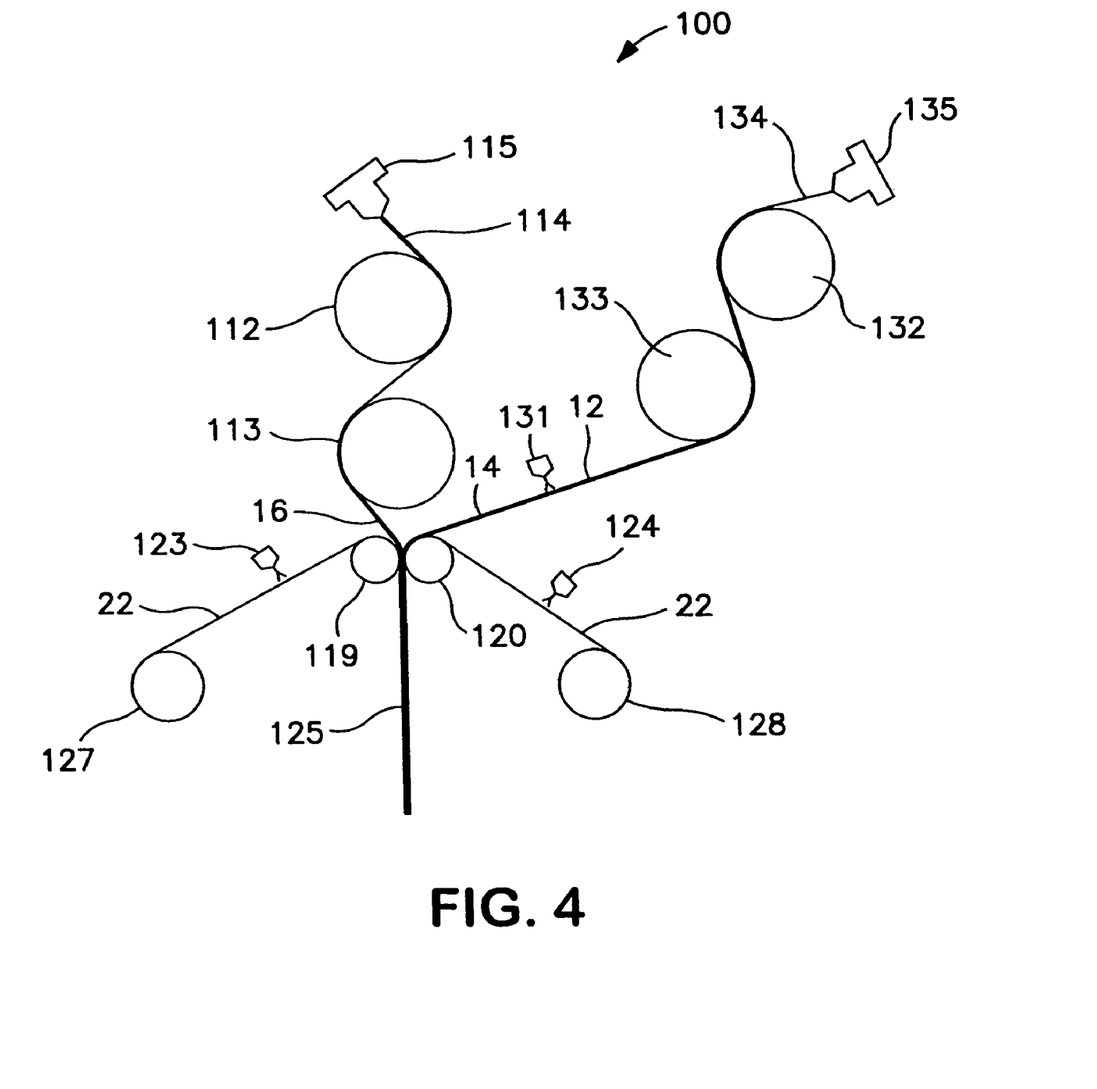
FIG. 4 is a schematic view of a process for making the elastic-powered laminate of the invention.

FIG. 4 illustrates an exemplary apparatus 100 for making an elastic-powered shrink laminate 125 which includes an elastic layer 16 adhesively bonded to a heat shrink layer 12, and two outer facing layers 22 adhesively bonded on both sides of the laminate. An extruder 115 is mounted for extruding continuous molten elastic filaments 114 downward from a die at a canted angle onto chilled positioning roller 112. Chilled positioning roller 112 ensures proper alignment through the remainder of the system as it spreads the filaments. As the filaments travel over the surface of chilled positioning roller 112, and over the chilled surface of chilled roll 113, the filaments are cooled and solidified.

A second extruder 135 is mounted for extruding a molten polymer film 134 onto chilled positioning roller 132 and over chilled roll 133, which cool and solidify the film. The elastic filaments 114 and film 134 are drawn toward a nip defined by rolls 119 and 120, which pulls the layers at a speed fast enough to stretch the filaments 114 (resulting in stretched elastic layer 16) and to stretch the film 134 (resulting in heat shrinkable layer 12). The speeds of the chill rolls 112, 113, 132 and 133 may be adjusted relative to the speed of nip rolls 119 and 120 to regulate the amount of stretching of elastic layer 16 and heat shrinkable layer 12. An adhesive spray head 131 deposits adhesive layer 14 onto the heat shrinkable layer 12 to ensure its bonding to the elastic layer 16.

In the embodiment shown, nonwoven facing layers 22 are unwound from rolls 127 and 128, coated with adhesive from spray heads 123 and 124, and combined with elastic layer 16 and heat shrinkable layer 12 to form elastic-powered shrink laminate 125. The nonwoven facing layers 22, which are present in some embodiments of the invention, may be spunbond webs, meltblown webs, bonded carded webs, film/nonwoven laminates or the like. The facing layers 22 may be formed from a wide variety of thermoplastic polymers, including without limitation ethylene homopolymers, ethylene-alpha olefin copolymers, propylene homopolymers, copolymers of propylene with ethylene or an alpha-olefin, polyamides, polyesters, polyurethanes and the like. When the elastic powered shrink laminate 125 is activated, the facing layers 22 will typically gather as the heat shrinkable layer 12 retracts and the elastic layer 16 recovers.

Figure 5:
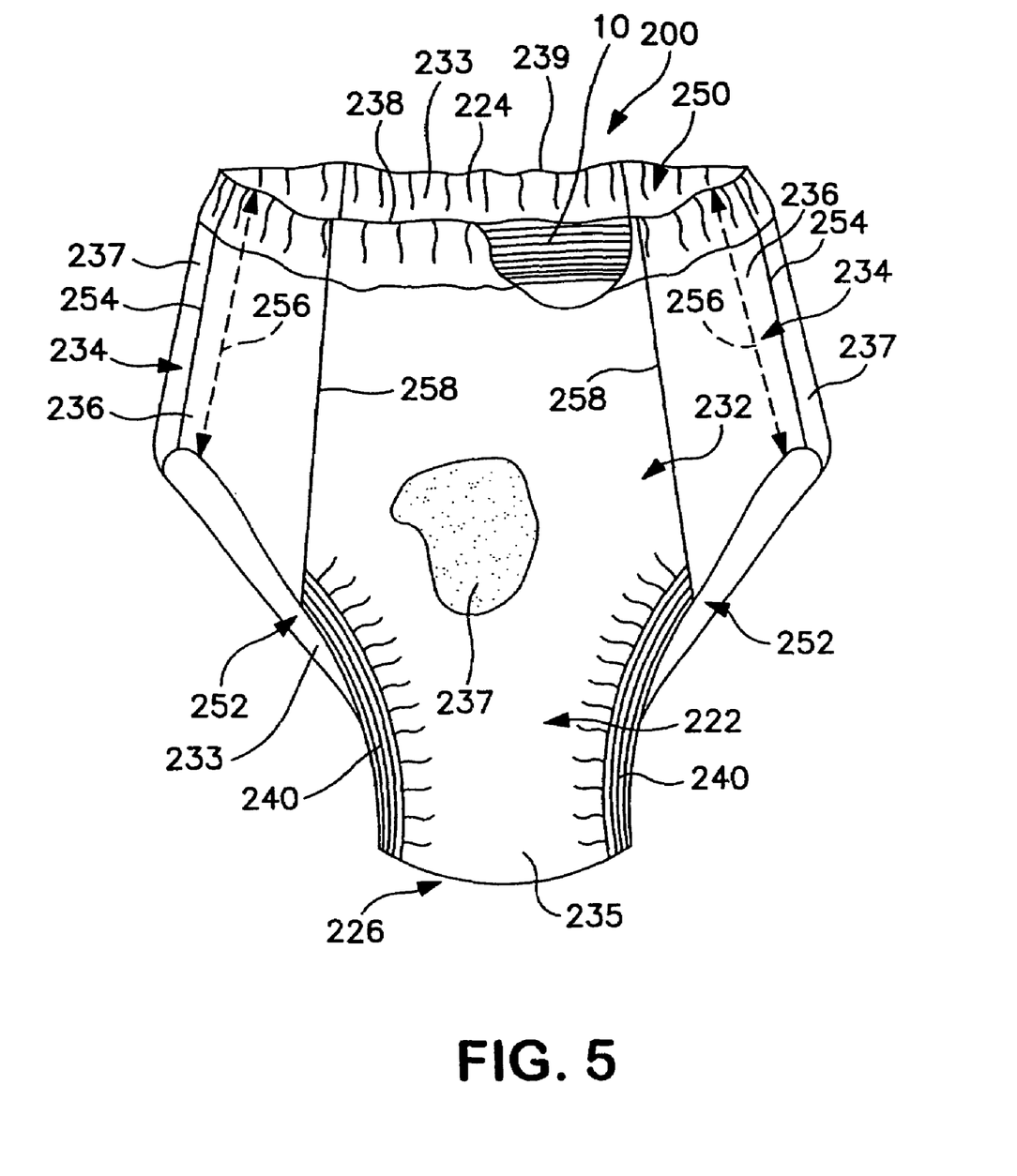
FIG. 5 is a partial cutaway perspective view of a personal care absorbent article incorporating the elastic-powered laminate in a waistband.

Referring to FIG. 5, a personal care absorbent article is illustrated which uses the elastic-powered shrink laminate 10 of the invention as a waistband. While the illustrated article is a training pant, the elastic-powered shrink laminate 10 of the invention may be used in a wide variety of personal care absorbent articles meeting the definition provided above.

Training pant 200 defines a three-dimensional pant configuration having a waist opening 250 and a pair of leg openings 252. The training pant includes a front region 222, a back region 224 and a crotch region 226. An absorbent chassis 232 extends from the front region through the crotch region and into the back region. The absorbent chassis 232 typically includes a liquid-permeable bodyside liner 233, a liquid-impermeable outer cover 235, and an absorbent core 237 between them.

A front waistband region 238 and back waistband region 239 are located longitudinally outward from the absorbent core 237 in the front and back regions of the article, respectively. Each waistband region may be defined by extensions of the bodyside liner 233, the outer cover 235, and an elastic-powered shrink laminate 10 of the invention. The elastic-powered shrink laminate 10 may be affixed to the bodyside liner 233 and/or outer cover 235 using adhesives and/or other bonding techniques conventionally used to install waistband materials, with the difference being that the elastic-powered shrink laminate 10 replaces the conventional waistband materials. When the elastic-powered shrink laminate 10 is activated for heat shrinkage, it causes shrinkage of the waistband regions 238 and 239 and localized gathering of the bodyside liner 233 and outer cover 235. The elastic-powered shrink laminate 10 may completely encircle the waist opening 250, or may be present in only part of the front waist region 238 and/or back waist region 239.

The illustrated training pant 200 also includes a pair of side panels 234, each including a front side panel portion 236 and a back side panel portion 237 joined at a seam 254. The side panels 234 can be joined to the chassis 232 along seam edges 258. Alternatively, the side panels 234 may be formed using extensions of the bodyside liner 233, the outer cover 235 or both, alone or in combination with other materials. The side panels 234 may be formed of elastic materials, or may include elastic materials. Each side panel 234 may extend the entire length 256 from the respective leg opening 252 to the waist opening 250 of the absorbent article.

The training pant 200 may also be equipped with leg elastics 240 at least partially surrounding each leg opening. In one embodiment of the invention, the elastic-powered shrink laminate 10 may also be incorporated into the leg elastics 240, in place of conventional materials. In another embodiment, the elastic-powered shrink laminate 10 may be incorporated into the side panels 234 to provide a snug fit around the wearer.

Except for the elastic-powered shrink laminate 10, the various components of the training pant 200 may be formed of conventional materials. The elastic-powered shrink laminate 10 is designed for incorporation into an otherwise conventional absorbent article, without requiring significant redesign of the article.

EXAMPLES

Using a process similar to the one illustrated in FIG. 4, except without the shrink film apparatus, two control samples were prepared in which an array of substantially parallel elastic filaments was stretched and laminated between two outer spunbond facing layers. The elastic filaments were formed of KRATON® 6673, which is a polymer blend based on styrene-(ethylene-butylene)-styrene triblock copolymers, further including polyethylene wax and a hydrocarbon tackifier. The filaments were extruded at a frequency of about 6 filaments per lateral centimeter from a die having a plurality of circular openings arranged in a row, using a melt temperature of 230-260° C. The filaments were stretched to about 5 times an original length before being combined with the spunbond facing layers. In the first control sample (Example 1) the elastic filaments had a diameter sufficient to provide a stretched basis weight of 15 grams/m$^2$ for the elastic layer. In the second control sample (Example 2), the elastic filaments had a diameter sufficient to provide a stretched basis weight of 30 grams/m$^2$ for the elastic layer.

The spunbond facing layers were formed of polypropylene and had a basis weight of about 17 grams/m$^2$ in a laid out (flat) state. Each spunbond layer was treated with 3 grams/m$^2$ of FINDLEY H2808-07 adhesive, available from Bostic Inc., using a melt spray process. The adhesive-coated spunbond facing layers and stretched elastic filaments were combined in a nip similar to the one illustrated in FIG. 4.

Examples 3-5 (inventive) were prepared using a similar process except that one of the spunbond facing layers was replaced with a heat shrinkable film. The heat shrinkable film was unwound from a roll (instead of being formed in-line, as suggested by FIG. 4). When preparing Examples 3-5, the 3 grams/m$^2$ of adhesive was applied directly only to the remaining spunbond facing layer. Due to the spaced-apart elastic filaments in the elastic layer, some of the adhesive transcended the elastic layer and assisted in bonding the heat shrinkable film. In Examples 3 and 4, the stretched elastic filaments defined an elastic layer having a basis weight of 15 grams/m$^2$. In Example 5, the stretched elastic filaments defined an elastic layer having a basis weight of 30 grams/m$^2$.

The heat shrinkable film used in Example 3 was formed from an experimental, single-site catalyzed ethylene-octene copolymer from Dow Chemical Co. having a density of 0.863 grams/cm$^3$ and a melt index (190° C.) of 2.5 grams/10 min. The heat shrinkable film had a thickness of 25 microns (after stretching), a basis weight of 20 grams/m$^2$, and was formed using a stretching temperature of 38° C. and a stretching ratio of 1.5.

The heat shrinkable film used in Example 4 was formed from an experimental propylene-based plastomer or elastomer ("PBPE") having a density of 0.858 grams/cm$^3$, a melt flow rate (230° C.) of 2 grams/10 min and an ethylene content of 15% by weight of the PBPE. These PBPE materials are taught in WO 03/040442, and U.S. Application 60/709,668 (filed 19 Aug. 2005), each of which is incorporated by reference. The heat shrinkable film had a thickness (after stretching) of 29 microns, a basis weight of 25 grams/m$^2$, and was formed using a stretching temperature of 38° C. and a stretching ratio of 1.65.

The heat shrinkable film used in Example 5 was a breathable two-layer film. The core layer (constituting about 98% by weight of the film thickness) contained 50% by weight particulate calcium carbonate (SCC 21382 from Standridge Color Corp.), 20% by weight of a commercial ethylene-alpha olefin copolymer having a density of 0.860 grams/cm$^3$ and a melt index of 3 grams/10 min (EXACT 5631 from Exxon-Mobil Chemical Co.) and 30% by weight of an experimental ethylene-octene copolymer having a density of 0.863 grams/cm$^3$ and a melt index of 5 grams/10 min (from Dow Chemical Co.). The skin layer (constituting about 2% of the film thickness) was formed from LD202.48, a branched low density polyethylene commercially available from Dow Chemical Co. The heat shrinkable film had a basis weight of 25.6 grams/m$^2$ and was formed using stretching temperatures of 35-80° C. and a stretching ratio of 4.48, using multiple stretch rollers.

The laminates of Examples 1-5 were heat activated by submerging them in a water bath at 71° C. for 30 seconds. Comparative Examples 1 and 2 exhibited heat shrinkage of 33% and 36%, respectively. Examples 3 and 4 exhibited heat shrinkages of 42% and 47%, respectively, significantly better than comparative Example 1 which also contained a 15 grams/m$^2$ elastic layer. Example 5 exhibited heat shrinkage of 41%, significantly better than comparative Example 2 which also utilized a 30 grams/m$^2$ elastic layer.

Following heat shrinkage, the laminates were cycle tested for elastic properties using the Cycle Testing procedure described below. As shown in Table 1 (below), the inventive Examples exhibited elastic properties similar to the comparative Examples prepared using an elastic layer having the same (15 gsm or 30 gsm) basis weight.

relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

TABLE 1

ELASTIC PROPERTIES

| | Cycle 1 | | | | | | | | Cycle 2 | | | | | | | |
|---|---|---|---|---|---|---|---|---|---|---|---|---|---|---|---|---|
| Example | 30% Up (g) | 50% Up (g) | 70% Up (g) | 100% Up (g) | 70% Down (g) | 50% Down (g) | 30% Down (g) | % Hyst | 30% Up (g) | 50% Up (g) | 70% Up (g) | 100% Up (g) | 70% Down (g) | 50% Down (g) | 30% Down (g) | % Set |
| POSTACTIVATION | | | | | | | | | | | | | | | | |
| 1 | 470 | 598 | 682 | 778 | 490 | 365 | 212 | 35.7 | 332 | 483 | 595 | 750 | 482 | 356 | 200 | 13.6 |
| 2 | 823 | 1051 | 1202 | 1371 | 934 | 717 | 441 | 29.4 | 623 | 889 | 1081 | 1334 | 918 | 698 | 416 | 11.4 |
| 3 | 418 | 555 | 674 | 888 | 472 | 325 | 178 | 35.6 | 277 | 435 | 582 | 860 | 461 | 313 | 165 | 13.3 |
| 4 | 433 | 580 | 702 | 924 | 470 | 325 | 174 | 38.2 | 290 | 455 | 604 | 896 | 459 | 313 | 160 | 15 |
| 5 | 848 | 1122 | 1317 | 1560 | 945 | 695 | 408 | 33.6 | 604 | 909 | 1147 | 1507 | 926 | 677 | 385 | 11.7 |

Test Method Procedures

Cycle Testing:

The materials were tested using a cyclical testing procedure to determine load loss and percent set. In particular, 2 cycle testing was utilized to 100 percent defined elongation. For this test, the sample size was 3 inch in the MD by 6 inch in the CD. The Grip size was 3 inch width. The grip separation was 4 inch. The samples were loaded such that the cross-direction of the sample was in the vertical direction. A preload of approximately 10-15 grams was set. The test pulled the sample to 100 percent elongation, and then immediately (without pause) returned to the zero. The results of the test data are all from the first and second cycles. The testing was done on a Sintech Corp. constant rate of extension tester 2/S with a Renew MTS mongoose box (controller) using TESTWORKS 4.07b software (Sintech Corp. of Cary, N.C.). The tests were conducted under ambient conditions.

Water Vapor Transmission Rate (WVTR):

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100%

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F\rho_{sat}(T)RH/A\rho_{sat}(T)(1-RH)$$

where:

F = The flow of water vapor in cc/min., $\rho_{sat}(T)$ = The density of water in saturated air at temperature T, RH = The relative humidity at specified locations in the cell, A = The cross sectional area of the cell, and, $\rho_{sat}(T)$ = The saturation vapor pressure of water vapor at temperature T.

The embodiments of the invention described herein are exemplary. Various modifications and improvements can be made without departing from the spirit and the scope of the invention. The scope of the invention is indicated by the appended claims. All changes that fall within the meaning and range of equivalents are intended to be embraced herein.

We claim:

1. An elastic-powered shrink laminate, comprising:
   a heat shrinkable layer comprising a thermoplastic polymer selected from the group consisting of ethylene homopolymers, ethylene-alpha olefin copolymers, propylene homopolymers, propylene copolymers with ethylene or an alpha-olefin, amorphous poly-alpha olefin, polyvinyl chlorides, and combinations thereof; and
   an elastic layer comprising an elastomer selected from the group consisting of styrene-diene block copolymers, styrene-olefin block copolymers, polyurethanes, copolyether esters, polyamide-polyether block copolymers, ethylene vinyl acetate copolymers, and combinations thereof;

wherein the heat shrinkable layer and elastic layer are continuously bonded together between the entirety of the interfacial regions therebetween with a substantially continuous adhesive layer when the elastic layer is in a dimensionally unstable, stretched state, and the elastic layer remains substantially in the stretched state prior to shrinkage of the heat shrinkable layer.

2. The laminate of claim 1, wherein the heat shrinkable layer has an activation temperature of about 28° C. to about 35° C.

3. The laminate of claim 1, wherein the heat shrinkable layer has an activation temperature of 55° C. or higher.

4. The laminate of claim 1, wherein the heat shrinkable layer has an activation temperature of 75° C. or higher.

5. The laminate of claim 1, wherein the heat shrinkable layer has a retraction potential of at least 25%.

6. The laminate of claim 1, wherein the heat shrinkable layer has a retraction potential of at least 50%.

7. The laminate of claim 1, wherein the heat shrinkable layer comprises a film.

8. The laminate of claim 7, wherein the film is a breathable film.

9. The laminate of claim 1, wherein the heat shrinkable layer comprises a nonwoven web.

10. The laminate of claim 1, wherein the heat shrinkable layer comprises a single-site catalyzed ethylene homopolymer or ethylene-alpha olefin copolymer.

11. The laminate of claim 1, wherein the elastic layer comprises a plurality of elastic filaments.

12. The laminate of claim 11, wherein the elastic filaments are disposed in a direction of orientation of the heat shrinkable layer.

13. The laminate of claim 11, wherein the elastic filaments are spaced apart and nonintersecting.

14. The laminate of claim 11, wherein the elastic filaments are substantially parallel to each other.

15. The laminate of claim 1, wherein the elastic layer is stretched to a stretched length at least 33% greater than an unstretched length when bonded to the heat shrinkable layer, and has a recovery potential of at least 25% of the stretched length.

16. The laminate of claim 1, wherein the elastic layer is stretched to a stretched length at least 100% greater than an unstretched length when bonded to the heat shrinkable layer, and has a recovery potential of at least 50% of the stretched length.

17. The laminate of claim 1, comprising two of the heat shrinkable layers bonded on both sides of the elastic layer.

18. The laminate of claim 1, further comprising a nonwoven facing layer bonded to at least one of the heat shrinkable layer and the elastic layer.

19. The laminate of claim 1, wherein the heat shrinkable layer and elastic layer are substantially continuously bonded together.

20. An elastic-power shrink laminate, comprising:
a heat shrinkable film layer comprising a thermoplastic polymer selected from the group consisting of ethylene homopolymers, ethylene-alpha olefin copolymers, propylene homopolymers, propylene copolymers with ethylene or an alpha-olefin, amorphous poly-alpha olefin, polyvinyl chlorides, and combinations thereof having a retraction potential of at least 20%; and
an elastic filament layer comprising an elastomer selected from the group consisting of styrene-diene block copolymers, styrene-olefin block copolymers, polyurethanes, copolyether esters, polyamide-polvether block copolymers, ethylene vinyl acetate copolymers, and combinations thereof;
wherein the heat shrinkable layer is continuously bonded to the elastic filament layer between the entirety of the interfacial regions therebetween with a substantially continuous adhesive layer when the elastic filament layer is stretched to a stretched length at least 25% greater than an unstretched length, the elastic filament layer has a recovery potential of at least 20% of the stretched length, and the elastic layer remains at about the stretched length prior to shrinkage of the heat shrinkable layer.

21. The laminate of claim 20, wherein the recovery potential of the elastic filament layer is about the same as the retraction potential of the heat shrinkable film layer.

22. The laminate of claim 20, wherein the recovery potential of the elastic filament layer exceeds the retraction potential of the heat shrinkable film layer.

23. The laminate of claim 22, wherein the recovery potential of the elastic filament layer is at least 1.5 times the retraction potential of the heat shrinkable layer.

24. The laminate of claim 22, wherein the recovery potential of the elastic filament layer is at least 2.0 times the retraction potential of the heat shrinkable layer.

25. An absorbent article comprising a liquid permeable bodyside liner, a substantially liquid impermeable outer cover, an absorbent core between them, and a waistband which includes an elastic-powered shrink laminate, wherein the elastic-powered shrink laminate comprises:
a heat shrinkable layer comprising a thermoplastic polymer selected from the group consisting of ethylene homopolymers, ethylene-alpha olefin copolymers, propylene homopolymers, propylene copolymers with ethylene or an alpha-olefin, amorphous poly-alpha olefin, polyvinyl chlorides, and combinations thereof; and
an elastic layer comprising an elastomer selected from the group consisting of styrene-diene block copolymers, styrene-olefin block copolymers, polyurethanes, copolyether esters, polyamide-polyether block copolymers, ethylene vinyl acetate copolymers, and combinations thereof, the elastic layer continuously bonded to the heat shrinkable layer between the entirety of the interfacial regions therebetween with a substantially continuous adhesive layer when the elastic layer is in a dimensionally unstable, stretched state;
the elastic layer remaining substantially in the stretched state prior to shrinkage of the heat shrinkable layer.

* * * * *

UNITED STATES PATENT AND TRADEMARK OFFICE
CERTIFICATE OF CORRECTION

| | |
|---|---|
| PATENT NO. | : 8,003,553 B2 |
| APPLICATION NO. | : 11/589669 |
| DATED | : August 23, 2011 |
| INVENTOR(S) | : Fitts, Jr. et al. |

Page 1 of 1

It is certified that error appears in the above-identified patent and that said Letters Patent is hereby corrected as shown below:

In the Claims

Column 16, Claim 20, line 12, after the word "polyamide-" delete "polvether" and replace with "polyether"

Signed and Sealed this
Fourteenth Day of January, 2014

Michelle K. Lee
*Deputy Director of the United States Patent and Trademark Office*